US011129557B2

(12) United States Patent
Li et al.

(10) Patent No.: US 11,129,557 B2
(45) Date of Patent: Sep. 28, 2021

(54) IMPLANTABLE MEDICAL DEVICE WITH CHEMICAL SENSOR

(71) Applicant: Cardiac Pacemakers, Inc., St. Paul, MN (US)

(72) Inventors: Yingbo Li, Woodbury, MN (US); Michael John Kane, St. Paul, MN (US); Jeffrey E. Stahmann, Ramsey, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 135 days.

(21) Appl. No.: 15/992,823

(22) Filed: May 30, 2018

(65) Prior Publication Data

US 2018/0344218 A1 Dec. 6, 2018

(30) Foreign Application Priority Data

May 31, 2017 (CN) .......................... 201710400287.0

(51) Int. Cl.
*A61B 5/1473* (2006.01)
*A61B 5/145* (2006.01)
(Continued)

(52) U.S. Cl.
CPC .......... *A61B 5/1473* (2013.01); *A61B 5/0031* (2013.01); *A61B 5/1459* (2013.01);
(Continued)

(58) Field of Classification Search
CPC ... A61B 5/1473; A61B 5/1459; A61B 5/0031; A61B 5/14546; A61B 5/686; A61B 5/14503; A61B 5/14507
See application file for complete search history.

(56) References Cited

U.S. PATENT DOCUMENTS

| 556,421 A | 3/1896 | Judge |
| 4,200,110 A | 4/1980 | Peterson et al. |

(Continued)

FOREIGN PATENT DOCUMENTS

| EP | 2967333 | 1/2016 |
| EP | 3492014 | 6/2019 |

(Continued)

OTHER PUBLICATIONS

Extended European Search Report for European Patent Application No. 18188253.1 dated Apr. 9, 2019 (10 pages).

(Continued)

*Primary Examiner* — Devin B Henson
*Assistant Examiner* — Joseph A Tombers
(74) *Attorney, Agent, or Firm* — Pauly, DeVries Smith & Deffner LLC

(57) ABSTRACT

Embodiments herein relate to chemical sensors for detecting a physiological analyte. In an embodiment, an implantable medical device including a chemical sensor for detecting an ion concentration in a bodily fluid is provided. The chemical sensor can include a sensing element having an outer barrier layer forming a top, a bottom, and opposed sides, where the top of the outer barrier layer can be created from a polymeric matrix permeable to sodium ions, potassium ions, and hydronium ions. An active agent can be disposed within the top of the outer barrier layer, the active agent having anti-inflammatory effects. The chemical sensor can include an optical excitation assembly configured to illuminate the sensing element. The chemical sensor can also include an optical detection assembly configured to receive light from the sensing element. Other embodiments are also included herein.

4 Claims, 5 Drawing Sheets

(51) Int. Cl.
    *A61B 5/00*     (2006.01)
    *A61B 5/1459*   (2006.01)

(52) U.S. Cl.
    CPC ...... *A61B 5/14546* (2013.01); *A61B 5/14503* (2013.01); *A61B 5/686* (2013.01)

(56) References Cited

U.S. PATENT DOCUMENTS

| | | |
|---|---|---|
| 4,321,057 A | 3/1982 | Buckles |
| 4,344,438 A | 8/1982 | Schultz et al. |
| 4,399,099 A | 8/1983 | Buckles |
| 4,680,268 A | 7/1987 | Clark |
| 4,704,029 A | 11/1987 | Van Heuvelen |
| 4,721,677 A | 1/1988 | Clark |
| 4,750,494 A | 6/1988 | King |
| 4,750,495 A | 6/1988 | Moore et al. |
| 4,890,621 A | 1/1990 | Hakky |
| 4,903,701 A | 2/1990 | Moore |
| 4,981,779 A | 1/1991 | Wagner |
| 5,001,054 A | 3/1991 | Wagner |
| 5,040,533 A | 8/1991 | Fearnot |
| 5,090,326 A | 2/1992 | Altenau et al. |
| 5,209,231 A | 5/1993 | Cote et al. |
| 5,267,151 A | 11/1993 | Ham et al. |
| 5,275,171 A | 1/1994 | Barcel |
| 5,312,439 A | 5/1994 | Loeb |
| 5,312,454 A | 5/1994 | Roline et al. |
| 5,330,718 A | 7/1994 | Hui et al. |
| 5,333,609 A | 8/1994 | Bedingham et al. |
| 5,342,406 A | 8/1994 | Thompson |
| 5,342,789 A | 8/1994 | Chick et al. |
| 5,355,880 A | 10/1994 | Thomas et al. |
| 5,378,432 A | 1/1995 | Bankert et al. |
| 5,419,329 A | 5/1995 | Smith et al. |
| 5,457,535 A | 10/1995 | Schmidtke et al. |
| 5,553,616 A | 9/1996 | Ham et al. |
| 5,556,421 A | 9/1996 | Prutchi et al. |
| 5,560,356 A | 10/1996 | Peyman |
| 5,605,152 A | 2/1997 | Slate et al. |
| 5,607,644 A | 3/1997 | Olstein et al. |
| 5,660,163 A | 8/1997 | Schulman et al. |
| 5,728,281 A | 3/1998 | Holmstrom et al. |
| 5,730,125 A | 3/1998 | Prutchi et al. |
| 5,741,211 A | 4/1998 | Renirie et al. |
| 5,797,898 A | 8/1998 | Santini et al. |
| 5,830,138 A | 11/1998 | Wilson |
| 5,833,603 A | 11/1998 | Kovacs et al. |
| 5,854,078 A | 12/1998 | Asher |
| 5,871,442 A | 2/1999 | Madarasz et al. |
| 5,902,326 A | 5/1999 | Lessar et al. |
| 5,958,782 A | 9/1999 | Bentsen et al. |
| 5,995,860 A | 11/1999 | Sun et al. |
| 6,002,954 A | 12/1999 | Van Antwerp et al. |
| 6,011,984 A | 1/2000 | Van Antwerp et al. |
| 6,040,194 A | 3/2000 | Chick et al. |
| 6,049,727 A | 4/2000 | Crothall |
| 6,070,093 A | 5/2000 | Oosta et al. |
| 6,097,139 A | 8/2000 | Tuck et al. |
| 6,122,536 A | 9/2000 | Sun et al. |
| 6,123,861 A | 9/2000 | Santini et al. |
| 6,125,290 A | 9/2000 | Miesel |
| 6,125,291 A | 9/2000 | Miesel et al. |
| 6,134,459 A | 10/2000 | Roberts et al. |
| 6,144,866 A | 11/2000 | Miesel et al. |
| 6,163,714 A | 12/2000 | Stanley et al. |
| 6,175,642 B1 | 1/2001 | Gobbi et al. |
| 6,187,599 B1 | 2/2001 | Asher et al. |
| 6,216,022 B1 | 4/2001 | Tyrrell et al. |
| 6,219,137 B1 | 4/2001 | Vo-Dinh |
| 6,232,130 B1 | 5/2001 | Wolf |
| 6,236,870 B1 | 5/2001 | Madarasz et al. |
| 6,256,522 B1 | 7/2001 | Schultz |
| 6,267,724 B1 | 7/2001 | Taylor et al. |
| 6,268,161 B1 | 7/2001 | Han et al. |
| 6,277,627 B1 | 8/2001 | Hellinga |
| 6,304,766 B1 | 10/2001 | Colvin, Jr. |
| 6,330,464 B1 | 12/2001 | Colvin et al. |
| 6,343,223 B1 | 1/2002 | Chin et al. |
| 6,344,340 B1 | 2/2002 | Dibner et al. |
| 6,368,274 B1 | 4/2002 | Van Antwerp et al. |
| 6,383,767 B1 | 5/2002 | Polak |
| 6,438,397 B1 | 8/2002 | Bosquet et al. |
| 6,442,409 B1 | 8/2002 | Peyman |
| 6,454,710 B1 | 9/2002 | Ballerstadt et al. |
| 6,466,821 B1 | 10/2002 | Pianca et al. |
| 6,491,639 B1 | 12/2002 | Turcott |
| 6,491,666 B1 | 12/2002 | Santini, Jr. et al. |
| 6,505,059 B1 | 1/2003 | Kollias et al. |
| 6,521,446 B2 | 2/2003 | Hellinga |
| 6,527,762 B1 | 3/2003 | Santini, Jr. et al. |
| 6,544,800 B2 | 4/2003 | Asher |
| 6,551,838 B2 | 4/2003 | Santini, Jr. et al. |
| 6,579,690 B1 | 6/2003 | Bonnecaze et al. |
| 6,594,092 B2 | 7/2003 | Von et al. |
| 6,594,510 B2 | 7/2003 | Madarasz et al. |
| 6,602,521 B1 | 8/2003 | Ting et al. |
| 6,625,479 B1 | 9/2003 | Weber et al. |
| 6,666,821 B2 | 12/2003 | Keimel et al. |
| 6,671,527 B2 | 12/2003 | Petersson et al. |
| 6,673,596 B1 | 1/2004 | Sayler et al. |
| 6,682,938 B1 | 1/2004 | Satcher, Jr. et al. |
| 6,694,158 B2 | 2/2004 | Polak |
| 6,711,423 B2 | 3/2004 | Colvin |
| 6,731,976 B2 | 5/2004 | Penn et al. |
| RE38,525 E | 6/2004 | Stanley et al. |
| 6,766,183 B2 | 7/2004 | Walsh |
| 6,771,993 B2 | 8/2004 | Rule et al. |
| 6,800,451 B2 | 10/2004 | Daniloff et al. |
| 6,804,544 B2 | 10/2004 | Van Antwerp et al. |
| 6,814,490 B1 | 11/2004 | Suhm et al. |
| 6,815,162 B2 | 11/2004 | Boukherroub et al. |
| 6,835,553 B2 | 12/2004 | Han et al. |
| 6,855,556 B2 | 2/2005 | Amiss et al. |
| 6,875,208 B2 | 4/2005 | Santini, Jr. et al. |
| 6,885,881 B2 | 4/2005 | Leonhardt |
| 6,885,883 B2 | 4/2005 | Parris et al. |
| 6,893,545 B2 | 5/2005 | Gotoh et al. |
| 6,912,078 B2 | 6/2005 | Kudrle et al. |
| 6,918,873 B1 | 7/2005 | Millar et al. |
| 6,928,325 B2 | 8/2005 | Zhu et al. |
| 6,937,900 B1 | 8/2005 | Pianca et al. |
| 6,944,488 B2 | 9/2005 | Roberts |
| 6,952,603 B2 | 10/2005 | Gerber et al. |
| 6,957,094 B2 | 10/2005 | Chance et al. |
| 6,976,982 B2 | 12/2005 | Santini, Jr. et al. |
| 6,978,182 B2 | 12/2005 | Mazar et al. |
| 7,016,714 B2 | 3/2006 | Colvin, Jr. et al. |
| 7,039,446 B2 | 5/2006 | Ruchti et al. |
| 7,070,590 B1 | 7/2006 | Santini, Jr. et al. |
| 7,107,086 B2 | 9/2006 | Reihl et al. |
| 7,133,710 B2 | 11/2006 | Acosta et al. |
| 7,134,999 B2 | 11/2006 | Brauker et al. |
| 7,164,948 B2 | 1/2007 | Struble et al. |
| 7,166,871 B2 | 1/2007 | Erchak |
| 7,174,212 B1 | 2/2007 | Klehn et al. |
| 7,225,024 B2 | 5/2007 | Zhu et al. |
| 7,236,821 B2 | 6/2007 | Cates et al. |
| 7,410,616 B2 | 8/2008 | Santini, Jr. et al. |
| 7,447,533 B1 | 11/2008 | Fang et al. |
| 7,449,246 B2 | 11/2008 | Kim et al. |
| 7,450,980 B2 | 11/2008 | Kawanishi |
| 7,471,290 B2 | 12/2008 | Wang et al. |
| 7,577,470 B2 | 8/2009 | Shah et al. |
| 7,632,234 B2 | 12/2009 | Manda et al. |
| 7,633,356 B2 | 12/2009 | Hamet et al. |
| 7,686,762 B1 | 3/2010 | Najafi et al. |
| 7,761,130 B2 | 7/2010 | Simpson et al. |
| 7,805,174 B2 | 9/2010 | Carpenter et al. |
| 7,809,441 B2 * | 10/2010 | Kane ................ A61B 5/14546 600/322 |
| 7,829,147 B2 | 11/2010 | Aitken et al. |
| 7,890,171 B2 | 2/2011 | Zhu et al. |
| 7,894,884 B2 | 2/2011 | Song et al. |
| 8,126,554 B2 | 2/2012 | Kane et al. |

(56) References Cited

U.S. PATENT DOCUMENTS

| | | |
|---|---|---|
| 8,131,364 B2 | 3/2012 | Zhu et al. |
| 8,141,489 B2 | 3/2012 | Belanger et al. |
| 8,160,670 B2 | 4/2012 | Ouyang et al. |
| 8,165,840 B2 | 4/2012 | Hatlestad et al. |
| 8,257,067 B2 | 9/2012 | Fukui et al. |
| 8,290,592 B2 | 10/2012 | Michael et al. |
| 8,303,511 B2 | 11/2012 | Eigler et al. |
| 8,378,453 B2 | 2/2013 | Fedorov et al. |
| 8,414,489 B2 | 4/2013 | Shah et al. |
| 8,435,604 B2 | 5/2013 | Aitken et al. |
| 8,527,067 B2 | 9/2013 | De Kock et al. |
| 8,571,659 B2 | 10/2013 | Kane et al. |
| 8,710,625 B2 | 4/2014 | Fedorov et al. |
| 8,827,899 B2 | 9/2014 | Farr et al. |
| 9,101,277 B2 | 8/2015 | Doerr |
| 9,357,968 B2 | 6/2016 | Hauer et al. |
| 9,693,714 B2 | 7/2017 | Dehennis et al. |
| 10,952,621 B2 | 3/2021 | Kane et al. |
| 11,089,983 B2 | 8/2021 | Li et al. |
| 2002/0016535 A1 | 2/2002 | Martin et al. |
| 2002/0026108 A1 | 2/2002 | Colvin |
| 2002/0033260 A1 | 3/2002 | Lungwitz et al. |
| 2002/0033454 A1 | 3/2002 | Cheng et al. |
| 2002/0035317 A1 | 3/2002 | Cheng et al. |
| 2002/0095075 A1 | 7/2002 | Madarasz et al. |
| 2002/0127626 A1 | 9/2002 | Daniloff et al. |
| 2002/0151812 A1 | 10/2002 | Scheiner et al. |
| 2003/0100040 A1 | 5/2003 | Bonnecaze et al. |
| 2003/0114735 A1 | 6/2003 | Silver et al. |
| 2003/0191376 A1 | 10/2003 | Samuels et al. |
| 2003/0208113 A1 | 11/2003 | Mault et al. |
| 2004/0023317 A1 | 2/2004 | Motamedi et al. |
| 2004/0030365 A1 | 2/2004 | Rubin |
| 2004/0059206 A1 | 3/2004 | Braig et al. |
| 2004/0073100 A1 | 4/2004 | Ballerstadt et al. |
| 2004/0087842 A1 | 5/2004 | Lakowicz et al. |
| 2004/0100376 A1 | 5/2004 | Lye et al. |
| 2004/0106953 A1 | 6/2004 | Yomtov et al. |
| 2004/0132172 A1 | 7/2004 | Cunningham et al. |
| 2004/0133079 A1 | 7/2004 | Mazar et al. |
| 2004/0147034 A1 | 7/2004 | Gore et al. |
| 2004/0161853 A1 | 8/2004 | Yang et al. |
| 2004/0176669 A1 | 9/2004 | Colvin, Jr. |
| 2004/0180379 A1 | 9/2004 | Van Duyne et al. |
| 2004/0180391 A1 | 9/2004 | Gratzl et al. |
| 2004/0186359 A1 | 9/2004 | Beaudoin et al. |
| 2004/0199062 A1 | 10/2004 | Petersson et al. |
| 2004/0206916 A1 | 10/2004 | Colvin, Jr. et al. |
| 2004/0215134 A1 | 10/2004 | Soykan et al. |
| 2004/0249311 A1 | 12/2004 | Haar et al. |
| 2004/0254438 A1 | 12/2004 | Chuck et al. |
| 2004/0260162 A1 | 12/2004 | Rohleder et al. |
| 2005/0027176 A1 | 2/2005 | Xie |
| 2005/0033133 A1 | 2/2005 | Kraft |
| 2005/0038329 A1 | 2/2005 | Morris et al. |
| 2005/0042704 A1 | 2/2005 | Alarcon et al. |
| 2005/0043894 A1 | 2/2005 | Fernandez |
| 2005/0065464 A1 | 3/2005 | Talbot et al. |
| 2005/0065556 A1 | 3/2005 | Reghabi et al. |
| 2005/0070768 A1 | 3/2005 | Zhu et al. |
| 2005/0070770 A1 | 3/2005 | Dirac et al. |
| 2005/0070771 A1 | 3/2005 | Rule et al. |
| 2005/0096587 A1 | 5/2005 | Santini et al. |
| 2005/0113657 A1 | 5/2005 | Alarcon et al. |
| 2005/0113658 A1 | 5/2005 | Jacobson et al. |
| 2005/0130249 A1 | 6/2005 | Parris et al. |
| 2005/0137481 A1 | 6/2005 | Sheard et al. |
| 2005/0148832 A1 | 7/2005 | Reghabi et al. |
| 2005/0149139 A1 | 7/2005 | Plicchi et al. |
| 2005/0154272 A1 | 7/2005 | Dirac et al. |
| 2005/0221276 A1 | 10/2005 | Rozakis et al. |
| 2005/0221277 A1 | 10/2005 | Kawanishi |
| 2005/0228226 A1 | 10/2005 | Muckner |
| 2006/0025748 A1 | 2/2006 | Ye |
| 2006/0076236 A1 | 4/2006 | Shah et al. |
| 2006/0217771 A1 | 9/2006 | Soykan et al. |
| 2006/0229694 A1 | 10/2006 | Schulman et al. |
| 2006/0253043 A1 | 11/2006 | Zhang et al. |
| 2007/0027495 A1 | 2/2007 | Gerber |
| 2007/0118056 A1 | 5/2007 | Wang et al. |
| 2007/0219628 A1 | 9/2007 | Shanley et al. |
| 2007/0252713 A1 | 11/2007 | Rondoni et al. |
| 2007/0270674 A1 | 11/2007 | Kane et al. |
| 2007/0270675 A1 | 11/2007 | Kane et al. |
| 2007/0275035 A1 | 11/2007 | Herman et al. |
| 2008/0033260 A1 | 2/2008 | Sheppard et al. |
| 2008/0046080 A1 | 2/2008 | Vanden et al. |
| 2008/0077190 A1 | 3/2008 | Kane |
| 2008/0082001 A1 | 4/2008 | Hatlestad et al. |
| 2008/0152283 A1 | 6/2008 | Nielsen et al. |
| 2008/0294209 A1 | 11/2008 | Thompson et al. |
| 2009/0018425 A1 | 1/2009 | Ouyang et al. |
| 2009/0024045 A1 | 1/2009 | Prakash et al. |
| 2009/0076353 A1* | 3/2009 | Carpenter ............ A61B 5/1459 600/310 |
| 2009/0124875 A1 | 5/2009 | Bentsen et al. |
| 2009/0221885 A1 | 9/2009 | Hall et al. |
| 2009/0312973 A1 | 12/2009 | Hatlestad et al. |
| 2010/0057057 A1 | 3/2010 | Hayter et al. |
| 2010/0149544 A1 | 6/2010 | Ghislain |
| 2010/0280578 A1 | 11/2010 | Skelton et al. |
| 2010/0292634 A1 | 11/2010 | Bilmes et al. |
| 2011/0024307 A1 | 2/2011 | Simpson et al. |
| 2011/0098547 A1* | 4/2011 | Zhu .................. A61B 5/14532 600/364 |
| 2011/0130666 A1 | 6/2011 | Dong et al. |
| 2013/0060105 A1 | 3/2013 | Shah et al. |
| 2013/0150689 A1 | 6/2013 | Shaw-klein |
| 2013/0184599 A1 | 7/2013 | Friedman et al. |
| 2013/0197332 A1 | 8/2013 | Lucisano et al. |
| 2014/0091945 A1 | 4/2014 | Rivas et al. |
| 2014/0155710 A1 | 6/2014 | Rowland et al. |
| 2014/0276164 A1 | 9/2014 | Thakur et al. |
| 2014/0286875 A1 | 9/2014 | Gamsey et al. |
| 2014/0357964 A1 | 12/2014 | Wisniewski et al. |
| 2014/0364758 A1 | 12/2014 | Schindhelm et al. |
| 2015/0057509 A1* | 2/2015 | Huffstetler ............ A61B 5/1459 600/309 |
| 2015/0164383 A1 | 6/2015 | Varsavsky et al. |
| 2015/0352229 A1 | 12/2015 | Brill et al. |
| 2016/0363550 A1 | 12/2016 | Koo et al. |
| 2016/0374597 A1 | 12/2016 | Stahmann |
| 2017/0215732 A1 | 8/2017 | Genier et al. |
| 2017/0245788 A1 | 8/2017 | Heikenfeld |
| 2018/0153451 A1 | 6/2018 | Heikenfeld et al. |
| 2018/0350468 A1 | 12/2018 | Friedman et al. |
| 2019/0029567 A1 | 1/2019 | Stahmann et al. |
| 2019/0046032 A1 | 2/2019 | Stahmann et al. |
| 2019/0059792 A1 | 2/2019 | Kane et al. |
| 2019/0125228 A1 | 5/2019 | Kane et al. |
| 2019/0167112 A1 | 6/2019 | Kane et al. |
| 2019/0167162 A1 | 6/2019 | Li et al. |

FOREIGN PATENT DOCUMENTS

| | | |
|---|---|---|
| EP | 3409203 | 4/2021 |
| JP | 2005287762 | 10/2005 |
| JP | 2005315871 | 11/2005 |
| JP | 2006507078 | 3/2006 |
| JP | 2006126715 | 5/2006 |
| JP | 2007525858 | 9/2007 |
| JP | 2009537247 | 10/2009 |
| WO | 9625978 | 8/1996 |
| WO | 9719188 | 5/1997 |
| WO | 9801071 | 1/1998 |
| WO | 9902651 | 1/1999 |
| WO | 0018289 | 4/2000 |
| WO | 0025862 | 5/2000 |
| WO | 0025863 | 5/2000 |
| WO | 0180728 | 11/2001 |
| WO | 2004039265 | 5/2004 |
| WO | 2004071291 | 8/2004 |
| WO | 2004081522 | 9/2004 |
| WO | 2004091719 | 10/2004 |

(56) References Cited

FOREIGN PATENT DOCUMENTS

| WO | 2004092713 | 10/2004 |
|---|---|---|
| WO | 2005074612 | 8/2005 |
| WO | 2006017169 | 2/2006 |
| WO | 2007110867 | 10/2007 |
| WO | 2007137037 | 11/2007 |
| WO | 2009038996 | 3/2009 |
| WO | 2013016573 | 1/2013 |
| WO | 2015048514 | 4/2015 |

OTHER PUBLICATIONS

Extended European Search Report for European Patent Application No. 18207668.7 dated Apr. 3, 2019 (7 pages).
Extended European Search Report for European Patent Application No. 18209525.7 dated Feb. 27, 2019 (12 pages).
Bakker, Eric et al., "Carrier-Based Ion-Selective Electrodes and Bulk Optodes. 1. General Characteristics," Chem. Rev. 1997, 97, 3083-3132 (50 pages).
Benco, John S. et al., "Optical Sensors for Blood Analytes," The Spectrum, vol. 14, Issue 4, pp. 4-11, Winter 2001 (8 pages).
Bender, J. W. et al., "The Use of Biomedical Sensors to Monitor Capsule Formation Around Soft Tissue Implants," Annals of Plastic Surgery, vol. 56, No. 1, Jan. 2006, pp. 72-77 (6 pages).
Buhlmann, Philippe et al., "Carrier-Based Ion-Selective Electrodes and Bulk Optodes. 2. Ionophores for Potentiometric and Optical Sensors," Chem. Rev. 1998, 98, 1593-1687 (95 pages).
"Communication Pursuant to Article 94(3) EPC," for European Patent Application No. 07762189.4 dated Mar. 24, 2009 (3 pages).
"Communication pursuant to Article 94(3) EPC," for European Patent Application No. 07762189.4 dated Mar. 16, 2010 (3 pages).
"Extended European Search Report," for European Patent Application No. 18174561.3 dated Aug. 28, 2018 (9 pages).
File History for U.S. Appl. No. 12/391,761.
"First Examination Report," for Australian Patent Application No. 2008302499 (dated Feb. 8, 2011 (1 page).
Han, In S. et al., "Constant-Volume Hydrogel Osmometer: A New Device Concept for Miniature Biosensors," Biomacromolecules, 3 2002, pp. 1271-1275 (5 pages).
He, Huarui et al., "Enantioselective Optodes," Analytica Chimica Acta, 246, pp. 251-257, 1991 (7 pages).
"International Search Report and Written Opinion," for PCT Application No. PCT/US2018/043225 dated Nov. 16, 2018 (11 pages).
"International Search Report and Written Opinion," for PCT Application No. PCT/US2018/047549 dated Oct. 26, 2018 (15 pages).
Kuwana, Eddy et al., "Sensing of pH in Multiply Scattering Media with Fluorescence Lifetime," Advanced Biomedical and Clinical Diagnostic Systems, Proceedings of SPIE, vol. 4958, pp. 32-42, 2003 (11 pages).
Lehn, J. M. et al., "[2]-Cryptates: Stability and Selectivity of Alkali and Akaline-Earth Macrobicycle Complexes," Journal of the American Chemical Society, Nov. 12, 1975 pp. 6700-6707 (8 pages).
Lima-Oliveira, Gabriel et al., "Patient Posture for Blood Collection by Venipuncture: Recall for Standardization After 28 Years," Brazilian Journal of Hematology and Hemotherapy 2017 <http://dx.doi.org/10.1016/j.bjhh.2017.01.004> (6 pages).
Messier, "The Joining of Materials," Nov. 2004 (58 pages).
"Microminiature Device Monitors Vital Electrolytes and Metabolites," John Glenn Biomedical Engineering Consortium, May 2002 (2 pages).
"Microminiature Monitor for Vital Electrolyte and Metabolite Levels of Astronauts—Status Report," John Glenn Biomedical Engineering Consortium NASA Glenn Research Center at Lewis Field, Apr. 2003 (5 pages). NASA Glenn Research Center at Lewis Field.
"Office Action," for Japanese Patent Application No. 2010-524940 dated Nov. 22, 2011 (8 pages) with English translation.
"PCT International Search Report and Written Opinion," for International Application No. PCT/US2007/068954, dated Oct. 31, 2007 (12 pages).
"Response to Communication Pursuant to Article 94(3) EPC," for European Patent Application No. 07762189.4 filed with the EPO Jul. 27, 2009 (8 pages).
Seelig, Mildred S. "Electrographic Patterns of Magnesium Depletion Appearing in Alcoholic Heart Disease," Annals of the New York Academy of Sciences, vol. 162, Article 2, 1969, pp. 906-917 (13 pages).
Shirreffs, S. M. "The Effect of Posture Change on Blood Volume, Serum Potassium, and Whole Body Electrical Impedance," Eur. J. Appl. Physiol. (1994)69:461-463 (3 pages).
Tohda, Koji et al., "A Microscopic, Continuous, Optical Monitor for Interstitial Electrolytes and Glucose," Chemphyschem 2003, pp. 155-160 (6 pages).
Tohda, Koji et al., "Micro-miniature Autonomous Optical Sensor Array for Monitoring Ions and Metabolites 1: Design, Fabrication, and Data Analysis," Analytical Sciences, Mar. 2006, vol. 22 pp. 383-388 (6 pages).
Tsai, Hc et al., "Simultaneous Determination of Renal Clinical Analytes in Serum using Hydrolase- and Oxidase-Encapsulated Optical Array Biosensors," Analytical Biochemistry 334 (2004) 183-192 (10 pages).
"Upconverting nanoparticles," Wikipeda.com accessed Jun. 12, 2017 (13 pages).
Voskerician, Gabriela et al., "Biocompatibility and Biofouling of MEMs Drug Delivery Devices," Biomaterials 24 (2003) 1959-1967 (9 pages).
Weisberg, Lawrence S. "Management of Severe Hyperkalemia," Crit Care Med 2008 vol. 36, No. 12 (6 pages).
Response to Communication Pursuant to Rule 69 EPC for European Patent Application No. 18174561.3 filed Jun. 4, 2019 (21 pages).
Extended European Search Report for European Patent Application No. 18202201.2 dated Jun. 28, 2019 (9 pages).
Anderson, J. M. et al., "Monocyte, Macrophage and foreign body giant cell interactions with molecularly engineered surfaces," Journal of Materials Science: Materials in Medicing 10 (1999) 579-588 (10 pages).
Anderson, James M. "Biological Responses to Materials," Annu. Rev. Mater. Res. 2001. 31:81-110 (30 pages).
Anderson, James M. et al., "Foreign Body Reaction to Biomaterials," Semin. Immunol. Apr. 2008; 20(2): 86-100 (27 pages).
Bridges, Amanda W. et al., "Anti-Inflammatory Polymeric Coatings for Implantable Biomaterials and Devices," Journal of Diabetes Science and Technology 2008;2(6):984-994 (11 pages).
File History for U.S. Appl. No. 11/856,850 downloaded Aug. 3, 2018 (229 pages).
He, Wei et al., "A Novel Anti-inflammatory Surface for Neural Electrodes," Adv. Mater. 2007, 19, 3529-3533 (5 pages).
Helton, Kristen L. et al., "Biomechanics of the Sensor-Tissue Interface-Effects of Motion, Pressure, and Design on Sensor Performance and the Foreign Body Response—Part I: Theoretical Framework," Journal of Diabetes Science and Technology 2011 ;5(3):632-646 (15 pages).
"International Preliminary Report on Patentability," for PCT Application No. PCT/US2008/075673 dated Mar. 24, 2010 (6 pages).
Koh, Ahyeon et al., "Glucose Sensor Membranes for Mitigating the Foreign Body Response," Journal of Diabetes Science and Technology 2011;5(5):1052-1059 (8 pages).
Koronczi, et al., "Development of a submicron optochemical potassium sensor with enhanced stability due to internal reference," Sensors and Actuators B, 51:188-195 (1998).
Novak, Matthew T. et al., "Modeling the relative impact of capsular tissue effects on implanted glucose sensor time lag and signal attenuation," Anal. Bioanal. Chem. Oct. 2010; 398(4):1695-1705 (22 pages).
Padmanabhan, Jagnnath et al., "Nanomaterials, Inflammation and Tissue Engineering," Wiley Interdiscip Rev Nanomed Nanobiotechnol. May 2015; 7(3):355-370 (23 pages).
"PCT International Search Report and Written Opinion from International Application No. PCT /US2008/075673, dated Nov. 28, 2008, pp. 1-13,".
Roger, Yvonne et al., "Grid-like surface structures in thermoplastic polyurethane induce anti-inflammatory and anti-fibrotic processes

(56) References Cited

OTHER PUBLICATIONS in bone marrow-derive dmesenchymal stem cells," Abstract Only Colloids and Surfaces B: Biointerfaces vol. 148, Dec. 2016, pp. 104-115 (4 pages).
Sharkawy, A. A. et al., "Engineering the tissue which encapsulates subcutaneous implants. I. Diffusion properties," Department of Biomedical Engineering, NSF Center for EmergingCardiovascular Technology, Duke University, Durham, North Carolina 1996 (12 pages).
Communication Pursuant to Article 94(3) EPC for European Patent Application No. 18174561.3 dated Jan. 27, 2020 (5 pages).
International Preliminary Report on Patentability for PCT Application No. PCT/US2018/043225 dated Feb. 6, 2020 (7 pages).
International Preliminary Report on Patentability for PCT Application No. PCT/US2018/047549 dated Mar. 5, 2020 (11 pages).
Response to Communication Pursuant to Rule 69 EPC for European Patent Application No. 18202201.2 filed Jan. 31, 2020 (22 pages).
Response to Communication Pursuant to Rule 69 EPC for European Patent Application No. 18209525.7 filed with the EPO Dec. 12, 2019 (33 pages).
Response to European Search Report for European Patent Application No. 18188253.1 filed Nov. 7, 2019 (14 pages).
Response to Extended European Search Report for European Patent Application No. 18207668.7 filed Nov. 29, 2019 (14 pages).
Partial European Search Report for European Patent Application No. 18188253.1 dated Jan. 7, 2019 (11 pages).
Non-Final Office Action for U.S. Appl. No. 16/038,737 dated Jun. 22, 2020 (46 pages).
Non-Final Office Action for U.S. Appl. No. 16/136,773 dated Jun. 1, 2020 (43 pages).
Non-Final Office Action for U.S. Appl. No. 16/136,875 dated May 27, 2020 (43 pages).
"Communication Pursuant to Article 94(3) EPC," for European Patent Application No. 18207668.7 dated Aug. 4, 2020 (5 pages).
"Final Office Action," for U.S. Appl. No. 16/038,737 dated Nov. 2, 2020 (15 pages).
"Final Office Action," for U.S. Appl. No. 16/136,875 dated Aug. 21, 2020 (10 pages).
"Non-Final Office Action," for U.S. Appl. No. 16/041,923 dated Jul. 23, 2020 (61 pages).
"Non-Final Office Action," for U.S. Appl. No. 16/106,623 dated Oct. 9, 2020 (60 pages).
"Non-Final Office Action," dated May 27, 2020 for U.S. Appl. No. 16/136,875, 43 pages.
"Response to Communication Pursuant to Article 94(3) EPC," for European Patent Application No. 18174561.3 filed Jul. 27, 2020 (11 pages).
"Response to Communication Pursuant to Rules 161(1) and 162 EPC," for European Patent Application No. 18773017.1 filed Sep. 30, 2020 (13 pages).
"Response to Final Rejection," dated Aug. 21, 2020 for U.S. Appl. No. 16/136,875, submitted via EFS-Web on Oct. 13, 2020, 12 pages.
"Response to Non-Final Rejection," dated Jul. 23, 2020 for U.S. Appl. No. 16/041,923, submitted via EFS-Web on Oct. 13, 2020, 12 pages.
"Response to Non-Final Rejection," dated Jun. 1, 2020 for U.S. Appl. No. 16/136,773, submitted via EFS-Web on Aug. 20, 2020, 10 pages.
"Response to Non-Final Rejection," dated Jun. 22, 2020 for U.S. Appl. No. 16/038,737, submitted via EFS-Web on Aug. 4, 2020, 10 pages.
"Response to Non-Final Rejection," dated May 27, 2020 for U.S. Appl. No. 16/136,875, submitted via EFS-Web on Jul. 22, 2020, 11 pages.
Communication Pursuant to Article 94(3) EPC for European Patent Application No. 18207668.7 dated Jan. 13, 2021 (4 pages).
Non-Final Office Action for U.S. Appl. No. 16/041,923 dated Feb. 2, 2021 (39 pages).
Non-Final Office Action for U.S. Appl. No. 16/136,875 dated Jan. 25, 2021 (12 pages).
Response to Final Rejection dated Nov. 2, 2020 for U.S. Appl. No. 16/038,737, submitted via EFS-Web on Feb. 2, 2021, 9 pages.
Response to Non-Final Rejection dated Feb. 2, 2021 for U.S. Appl. No. 16/041,923, submitted via EFS-Web on Mar. 17, 2021, 12 pages.
Response to Non-Final Rejection dated Jan. 25, 2021 for U.S. Appl. No. 16/136,875, submitted via EFS-Web on Mar. 17, 2021, 12 pages.
Response to Non-Final Rejection dated Oct. 9, 2020 for U.S. Appl. No. 16/106,623, submitted via EFS-Web on Jan. 8, 2021, 21 pages.
Communication Pursuant to Article 94(3) EPC for European Patent Application No. 18209525.7 dated Dec. 8, 2020 (5 pages).
Notice of Allowance for U.S. Appl. No. 16/136,773 dated Nov. 18, 2020 (17 pages).
Response to Communication Pursuant to Article 94(3) EPC for European Patent Application No. 18207668.7 filed Dec. 11, 2020 (65 pages).
Response to Final Rejection dated Aug. 21, 2020 and Advisory Action received on Oct. 19, 2020 for U.S. Appl. No. 16/136,875, submitted via EFS-Web on Nov. 20, 2020, 14 pages.
"Non-Final Office Action," for U.S. Appl. No. 16/038,737 dated Mar. 24, 2021 (14 pages).
"Notice of Allowance," for U.S. Appl. No. 16/136,875 dated Apr. 15, 2021 (13 pages).
"Response to Communication Pursuant to Article 94(3) EPC," for European Patent Application No. 18209525.7 filed Apr. 15, 2021 (10 pages).
"Final Office Action," for U.S. Appl. No. 16/041,923 dated Jul. 9, 2021 (29 pages).
"Response to Communication Pursuant to Article 94(3) EPC," for European Patent Application No. 18207668.7 filed May 21, 2021 (32 pages).
"Response to Non-Final Rejection," dated Mar. 24, 2021 for U.S. Appl. No. 16/038,737, submitted via EFS-Web on Jun. 18, 2021, 11 pages.

* cited by examiner

IMPLANTABLE MEDICAL DEVICE WITH CHEMICAL SENSOR

This application claims the benefit of China Patent Application No. 201710400287.0, filed May 31, 2017, the content of which is herein incorporated by reference in its entirety.

FIELD

Embodiments herein relate to implantable chemical sensors for detecting a physiological analyte and medical devices including the same.

BACKGROUND

Implantable medical devices (IMDs) are often used to provide treatment or therapy to patients. Certain physiological analytes impact many of the problems that IMDs are designed to treat. As one example, potassium ion concentrations can affect a patient's cardiac rhythm. Therefore, medical professionals frequently evaluate physiological potassium ion concentration when diagnosing a cardiac rhythm problem. However, measuring physiological concentrations of analytes, such as potassium, generally requires drawing blood from the patient. Blood draws are commonly done at a medical clinic or hospital and therefore generally require the patient to physically visit a medical facility. As a result, despite their significance, physiological analyte concentrations are frequently measured only sporadically.

SUMMARY

Embodiments herein relate to chemical sensors for detecting a physiological analyte.

In a first aspect, an implantable medical device including a chemical sensor is provided. The chemical sensor can be configured to detect an ion concentration in a bodily fluid. The chemical sensor can include a sensing element. The sensing element can include an outer barrier layer forming a top, a bottom, and opposed sides of the sensing element. The top of the outer barrier layer can be created from a polymeric matrix permeable to physiological analytes. An active agent can be disposed within the top of the outer barrier layer, the active agent having anti-inflammatory effects. The chemical sensor can include an optical excitation assembly configured to illuminate the sensing element. The chemical sensor can also include an optical detection assembly configured to receive light from the sensing element.

In addition to one or more of the preceding or following aspects, or in the alternative to some aspects, in a second aspect, the bottom and opposed sides of the outer barrier layer can include or be a polymeric matrix permeable to sodium ions, potassium ions, hydronium ions, urea and creatinine.

In addition to one or more of the preceding or following aspects, or in the alternative to some aspects, in a third aspect, the bottom and opposed sides of the outer barrier layer can include or be a material that is impermeable to sodium ions, potassium ions, and hydronium ions.

In addition to one or more of the preceding or following aspects, or in the alternative to some aspects, in a fourth aspect, the chemical sensor is coupled to the implantable housing and the implantable housing defines a recessed pan into which the sensing element fits.

In addition to one or more of the preceding or following aspects, or in the alternative to some aspects, in a fifth aspect, the implantable housing defines an aperture occluded by a transparent member, the aperture disposed at the bottom of the recessed pan, the sensing element in optical communication with the excitation assembly and the detection assembly through the transparent member.

In addition to one or more of the preceding or following aspects, or in the alternative to some aspects, in a sixth aspect, an aqueous solution is disposed within at least a portion of the sensing element, aqueous solution including potassium ions at a concentration from about 3.0 to about 6.0 mmol/L.

In addition to one or more of the preceding or following aspects, or in the alternative to some aspects, in a seventh aspect, the outer barrier layer surrounds an interior volume and the chemical sensor further includes active-agent releasing particles disposed within the interior volume of the outer barrier layer.

In addition to one or more of the preceding or following aspects, or in the alternative to some aspects, in an eighth aspect, the outer barrier layer surrounds an interior volume and the active-agent releasing particles include a first particle type configured to release an anti-inflammatory agent during a first period of time and a second particle type configured to release an angiogenic agent after the passage of the first period of time.

In addition to one or more of the preceding or following aspects, or in the alternative to some aspects, in a ninth aspect, the outer barrier layer surrounds an interior volume and the sensing element further includes a first indicator bead and a second indicator bead disposed within the interior volume.

In addition to one or more of the preceding or following aspects, or in the alternative to some aspects, in a tenth aspect, the active agent is or includes a corticosteroid.

In addition to one or more of the preceding or following aspects, or in the alternative to some aspects, in an eleventh aspect, the polymeric matrix includes a polymer selected from the group consisting of hydroxyethylmethacrylate, cellulose, polyvinyl alcohol, dextran, polyurethanes, quaternized polystyrenes, sulfonated polystyrenes, polyacrylamides, polyhydroxyalkyl acrylates, polyvinyl pyrrolidones, polyamides, polyesters, and mixtures and copolymers thereof.

In addition to one or more of the preceding or following aspects, or in the alternative to some aspects, in a twelfth aspect, the polymeric matrix is or includes poly hydroxyethylmethacrylate.

In addition to one or more of the preceding or following aspects, or in the alternative to some aspects, in a thirteenth aspect, the device includes an opaque cover layer disposed on the top side of the sensing element, the opaque cover layer including an ion permeable polymeric matrix.

In addition to one or more of the preceding or following aspects, or in the alternative to some aspects, in a fourteenth aspect, the chemical sensor is configured to detect an ion selected from the group consisting of potassium, sodium, chloride, calcium, magnesium, lithium and hydronium.

In addition to one or more of the preceding or following aspects, or in the alternative to some aspects, in a fifteenth aspect, the excitation assembly includes a light source, the light source comprising a light emitting diode.

In addition to one or more of the preceding or following aspects, or in the alternative to some aspects, in a sixteenth aspect, the detection assembly includes a component selected from the group consisting of a photodiode, a phototransistor, a charge-coupled device (CCD), a junction field effect transistor (JFET) optical sensor, a complementary metal-oxide semiconductor (CMOS) optical sensor, an integrated photo detector integrated circuit, and a light to voltage converter.

In addition to one or more of the preceding or following aspects, or in the alternative to some aspects, in a seventeenth aspect, an implantable medical device with a chemical sensor is included. The chemical sensor can be configured to detect an ion concentration in a bodily fluid. The chemical sensor can include a sensing element. The sensing element can include an outer barrier layer forming a top, a bottom, and opposed sides of the sensing element. The top of the outer barrier layer can be created from a polymeric matrix permeable to physiological analytes. The chemical sensor can include an optical excitation assembly configured to illuminate the sensing element. The chemical sensor can also include an optical detection assembly configured to receive light from the sensing element. The chemical sensor can also include a drug-eluting material with an active agent disposed therein positioned around the opposed sides of the sensing element. The active agent can include an active agent having anti-inflammatory effects.

In addition to one or more of the preceding or following aspects, or in the alternative to some aspects, in an eighteenth aspect, the drug-eluting material with an active agent disposed therein forms a ring around the sensing element.

In addition to one or more of the preceding or following aspects, or in the alternative to some aspects, in an nineteenth aspect, the drug-eluting material with an active agent disposed therein forms one or more discrete depots around the sensing element.

In addition to one or more of the preceding or following aspects, or in the alternative to some aspects, in an twentieth aspect, an active agent is disposed within a portion of the sensing element.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Medical professionals frequently need to evaluate chemical analyte concentrations of a patient when assessing the patient's condition and/or diagnosing a problem. However, measuring physiological concentrations of analytes, such as potassium amongst others, generally requires drawing blood from the patient. Blood draws are commonly done at a medical clinic or hospital and therefore generally require the patient to physically visit a medical facility. As a result, despite their significance, physiological analyte concentrations are frequently measured only sporadically.

Implanted chemical sensors offer the promise of being able to gather data on analyte concentrations even while a patient is away from a medical treatment facility. For example, implanted chemical sensors can measure analyte concentrations continuously or semi-continuously providing a far richer data set for a medical professional to evaluate.

However, implanted chemical sensors can be hindered in their ability to function properly over a relatively long period of time. For example, a patient's foreign body response can result in the infiltration by fibroblasts which multiply and lay down collagen that begins to form an avascular connective tissue envelope or "pocket". This process can continue for months and can result in the complete encasement of the chemical sensor and/or medical device in an avascular pocket with walls that are 50 $\mu$m to 200 $\mu$m thick. This avascular pocket can adversely affect the functioning of the medical device.

Embodiments herein, however, can include elute an active agent in order to attenuate the foreign body response and prevent or reduce the thickness of the avascular pocket. Improving the local communication between sensor and physiologic environment.

Figure 1:
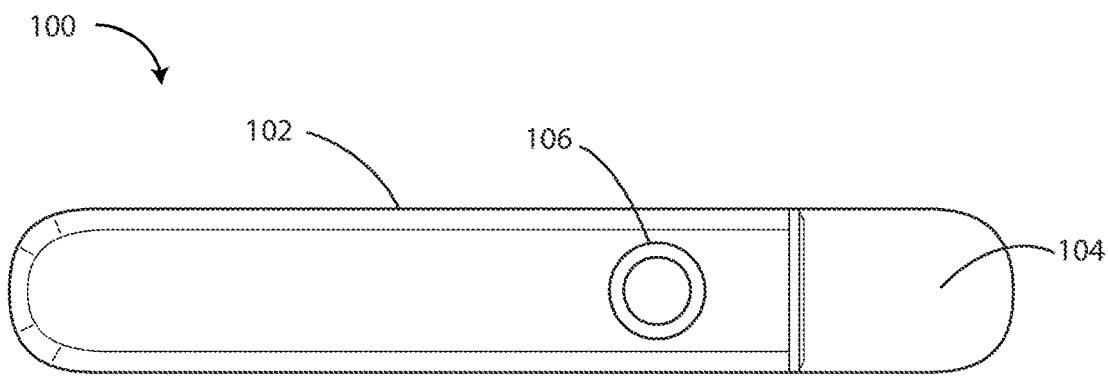
FIG. 1 is a schematic top view of an implantable medical device in accordance with the embodiments herein.

Referring now to FIG. 1, an implantable medical device (IMD) 100 is shown in accordance with the embodiments herein. The IMD 100 can include an implantable housing 102 and a header 104 coupled to the implantable housing 102. Various materials can be used. However, in some embodiments, the housing 102 can be formed of a material such as a metal, ceramic, a polymer, or a composite. The header 104 can be formed of various materials, but in some embodiments the header 104 can be formed of a translucent polymer such as an epoxy material. In some embodiments the header 104 can be hollow. In other embodiments the header 104 can be filled with components and/or structural materials such as epoxy or another material such that it is non-hollow. The IMD 100 can also include a chemical sensor 106 coupled to the implantable housing 102. Chemical sensor 106 can be configured to detect an ion concentration of a bodily fluid when implanted in the body. Bodily fluids can include blood, interstitial fluid, serum, lymph, serous fluid, cerebrospinal fluid, and the like. In some embodiments chemical sensor 106 can be configured to detect one or more of an electrolyte, a protein, a sugar, a hormone, a peptide, an amino acid and a metabolic product. In some embodiments, the chemical sensor 106 can be configured to detect an ion selected from the group consisting of potassium, sodium, chloride, calcium, magnesium, lithium, hydronium, hydrogen phosphate, bicarbonate, and the like. However, many other analytes are also contemplated herein.

It will be appreciated that chemical sensor 106 can be positioned at any location along IMD 100, including along the implantable housing 102 and along the header 104. The IMD 100 can take on various dimensions. In a particular embodiment herein it can be approximately 2 to 3 inches in length, 0.4 to 0.6 inches wide, and 0.15 to 0.35 inches thick. However, in some embodiments, the IMD 100 can be about 0.25, 0.5, 1.0, 2.0, 3.0, 4.0, or 5.0 inches in length. In some embodiments the length can be in a range wherein any of the foregoing lengths can serve as the upper or lower bound of the range, provided that the upper bound is greater than the lower bound. In some embodiments, the IMD 100 can be about 0.25, 0.5, 0.75, 1.0, or 2.0 inches in width. In some embodiments the length can be in a range wherein any of the foregoing widths can serve as the upper or lower bound of the range, provided that the upper bound is greater than the lower bound. In some embodiments, the IMD 100 can be about 0.10, 0.25, 0.50, 0.75 or 1.0 inches thick. In some embodiments the thickness can be in a range wherein any of the foregoing thicknesses can serve as the upper or lower bound of the range, provided that the upper bound is greater than the lower bound.

Figure 2:
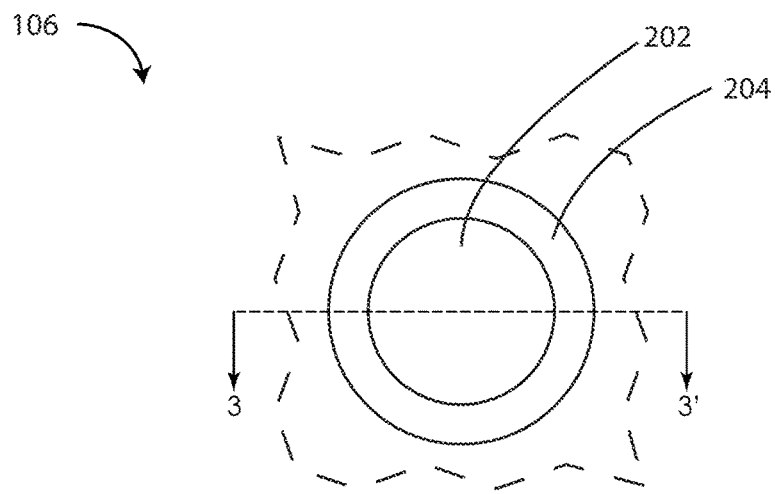
FIG. 2 is a schematic view of a chemical sensor in accordance with various embodiments herein.

Referring now to FIG. 2, a top-down view of chemical sensor 106 is shown magnified with respect to FIG. 1. Chemical sensor 106 can include a sensing element 202 and an active agent eluting material 204 (or active agent eluting matrix) disposed around the outer perimeter of sensing element 202. In some embodiments, active agent eluting material 204 forms a ring structure around the outer perimeter of sensing element 202. It will be appreciated that chemical sensor 106 can take on many geometric shapes and sizes.

Figure 3:
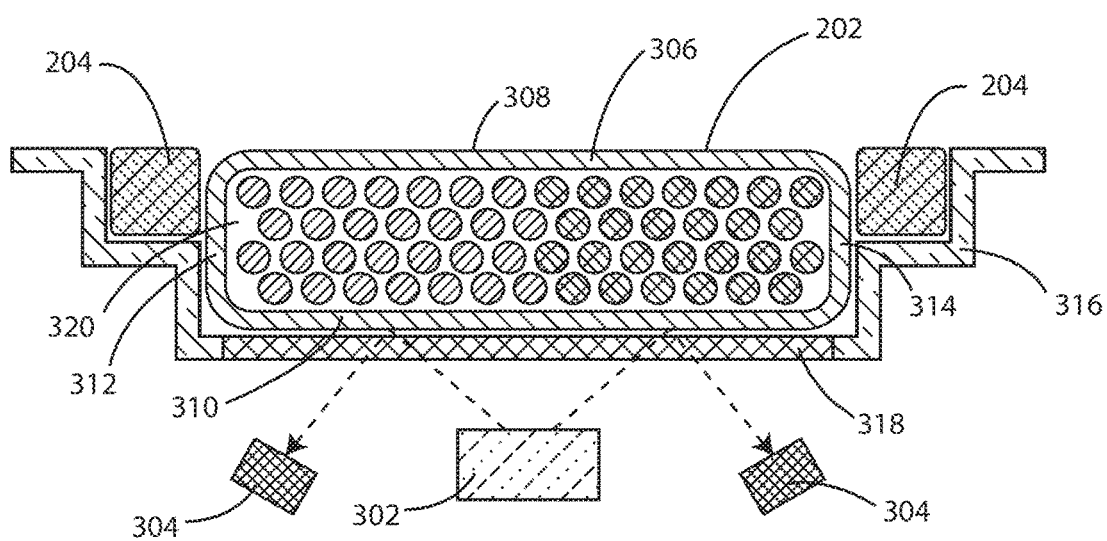
FIG. 3 is a cross-sectional view of a chemical sensor taken along line 3-3' of FIG. 2.

Referring now to FIG. 3, a cross-sectional view of chemical sensor 106 along line 3-3' of FIG. 2 is shown. Chemical sensor 106 can include, but not be limited to, sensing element 202, active agent eluting material 204 disposed around the outer perimeter of sensing element 202, optical excitation assembly 302, and optical detection assembly 304. FIG. 3 shows an optical chemical sensor. However, in other embodiments the chemical sensor can be a potentiometric chemical sensor.

The sensing element 202 can include an outer barrier layer 306 formed, in full or in part, from a permeable material, such as an ion permeable polymeric matrix material. Exemplary materials for the outer barrier layer 306 are described in greater detail below. Outer barrier layer 306 can form a top 308, a bottom 310, and opposed sides 312 and 314 to surround an interior volume 320 of sensing element 202. Bottom 310 and opposed sides 312 and 314 of outer barrier layer 306 will be discussed in more detail below in reference to FIGS. 7-9. Briefly, however, they can be formed of the same material as the top 308, or they can be formed from a different material. In some embodiments, at least the top 308 of outer barrier layer 306 can be permeable to sodium ions, potassium ions, hydronium ions, creatinine, urea, and the like. Outer barrier layer 306 can also include an active agent disposed therein including, but not limited to anti-inflammatory agents, angiogenic agents, and the like. Exemplary active agents are described in greater detail below.

In will be appreciated, however, that bottom 310 may or may not be a discrete layer. For example, in some embodiments, bottom 310 and the transparent member 318 may be fused with different material or fused as one layer with same type of material.

The implantable housing 102 can include a recessed pan 316 into which the sensing element 202 fits. In some embodiments, the top of the recessed pan 316 can be substantially flush with the top of the sensing element 202.

In some embodiments, implantable housing 102 can define an aperture occluded by a transparent member 318. The transparent member 318 can be a glass (including but not limited to borosilicate glasses), a polymer or other transparent material. The aperture can be disposed at the bottom of the recessed pan 316. The aperture can provide an interface allowing for optical communication between sensing element 202 and the optical excitation 302 and optical detection 304 assemblies.

It will be appreciated that outer barrier layer, or portions thereof such as the bottom 310, can be made from a transparent polymer matrix material to allow for optical communication between the sensing element 202 and optical excitation 302 and optical detection 304 assemblies.

The optical excitation assembly 302 can be designed to illuminate the sensing element 202. Optical excitation assembly 302 can include a light source such as a light emitting diode (LED), vertical-cavity surface-emitting lasers (VCSELs), electroluminescent (EL) devices, and the like. Optical detection assembly 304 can include a component selected from the group consisting of a photodiode, a phototransistor, a charge-coupled device (CCD), a junction field effect transistor (JFET) optical sensor, a complementary metal-oxide semiconductor (CMOS) optical sensor, an integrated photo detector integrated circuit, a light to voltage converter, and the like. Optical excitation 302 and optical detection 304 assemblies are discussed in further detail below.

Figure 4:
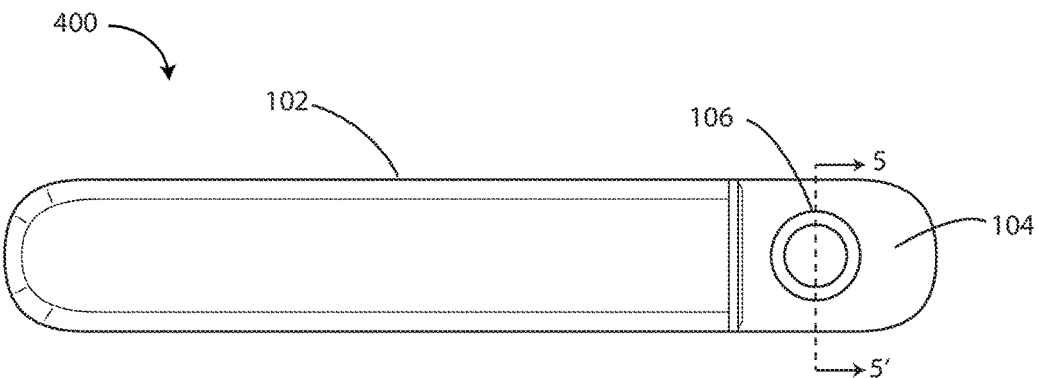
FIG. 4 is a schematic top view of an implantable medical device in accordance with additional embodiments herein.
Figure 5:
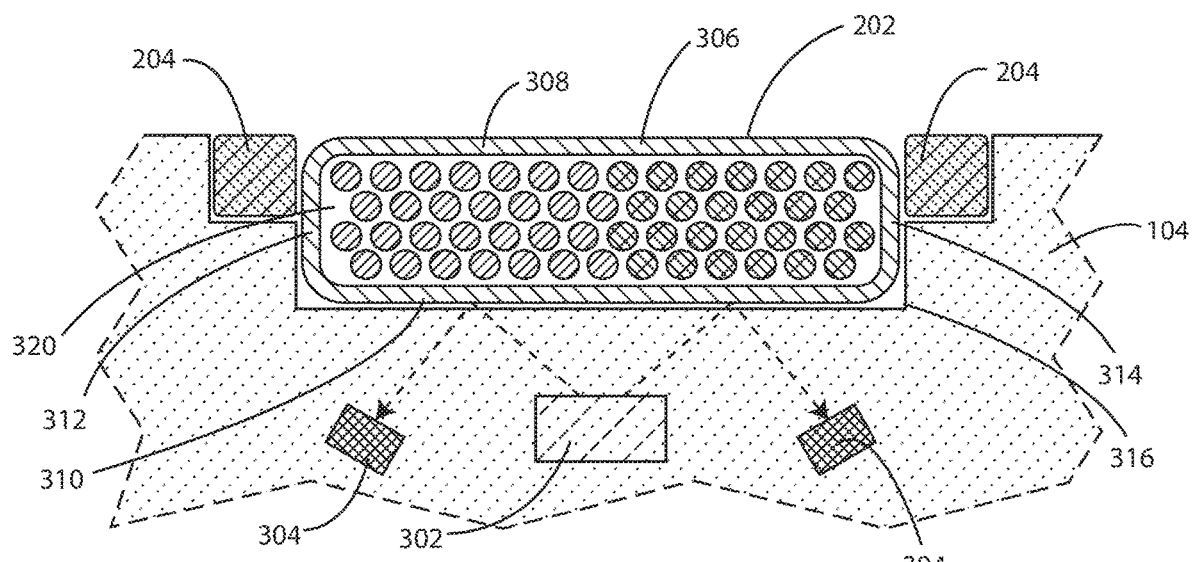
FIG. 5 is a cross-sectional view of a chemical sensor taken along line 5-5' of FIG. 4.

Referring now to FIGS. 4 and 5, implantable medical device 400 is shown in accordance with additional embodiments herein. FIG. 4 shows IMD 400 with an implantable housing 102 coupled to a header 104. The chemical sensor 106 is shown coupled to the header 104. Referring now to FIG. 5, IMD 400 is shown in cross-section along line 5-5' of FIG. 4. FIG. 5 shows chemical sensor 106 having many of the features of chemical sensor 106 as presented in FIG. 3. However, FIG. 5 shows sensing element 202 coupled within a recessed pan 316 of the header 104.

Figure 6:
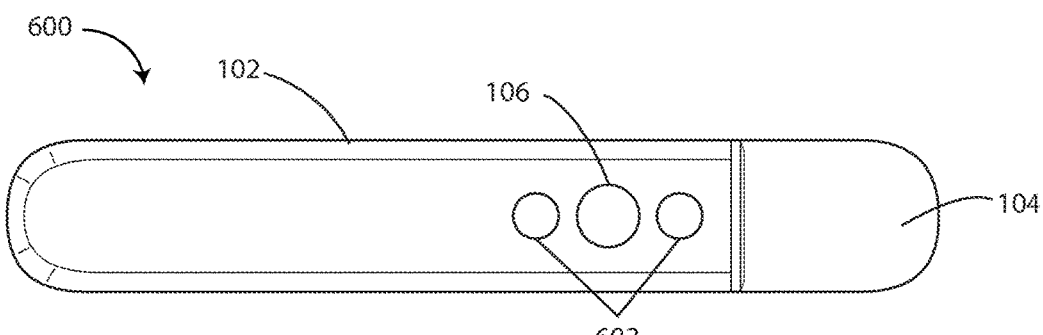
FIG. 6 is a schematic top view of an implantable medical device in accordance with additional embodiments herein.

Referring now to FIG. 6, IMD 600 is shown in accordance with additional embodiments herein. IMD 600 can include an implantable housing 102 coupled to a header 104. IMD 600 can also include a chemical sensor 106 located in implantable hosing 104, or alternatively in header 104. Chemical sensor 106 is shown disposed between two depots 602 of active agent dispersed within an active agent eluting material. In some embodiments, the two depots 602 contain the same active agent. In some embodiments, the two depots 602 contain different active agents. Suitable active agents for use with embodiments herein are discussed further below. In some embodiments, the active agent dispersed within an active agent eluting material can form a ring around the chemical sensor.

Figure 7:
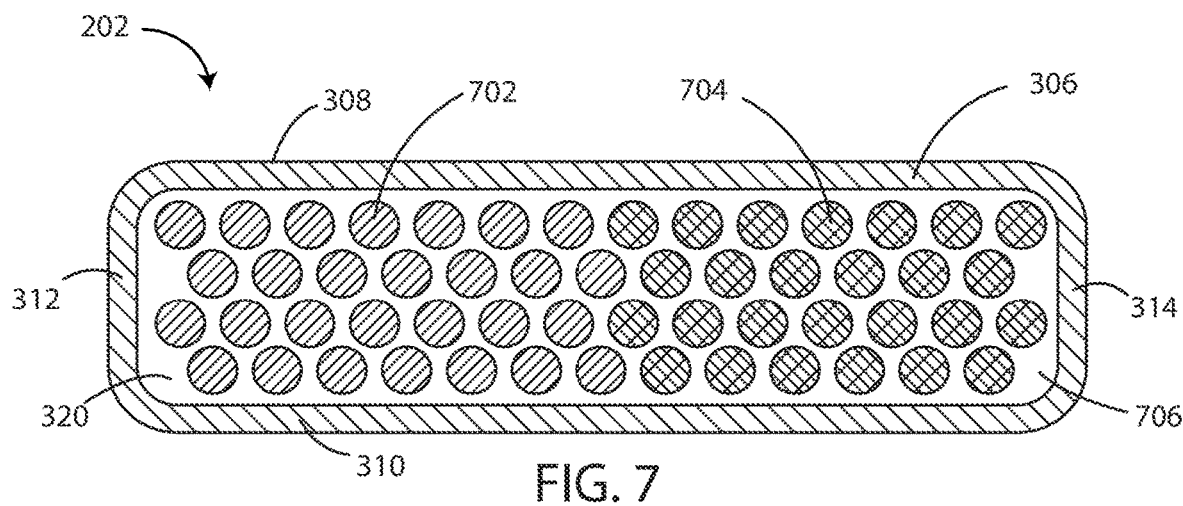
FIG. 7 is a schematic cross-sectional view of a sensing element in accordance with the embodiments herein.
Figure 8:
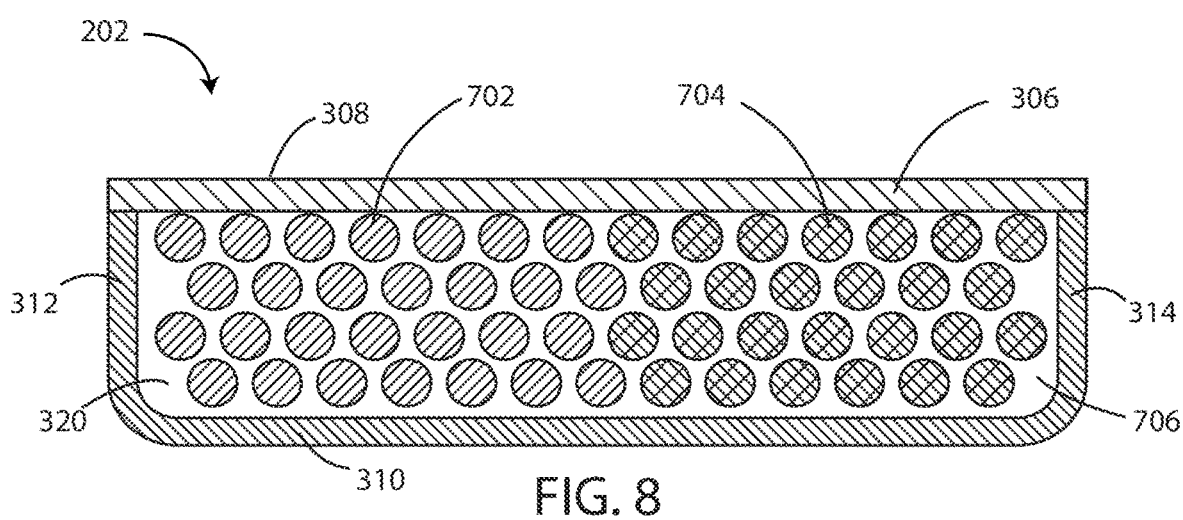
FIG. 8 is a schematic cross-sectional view of a sensing element in accordance with additional embodiments herein.
Figure 9:
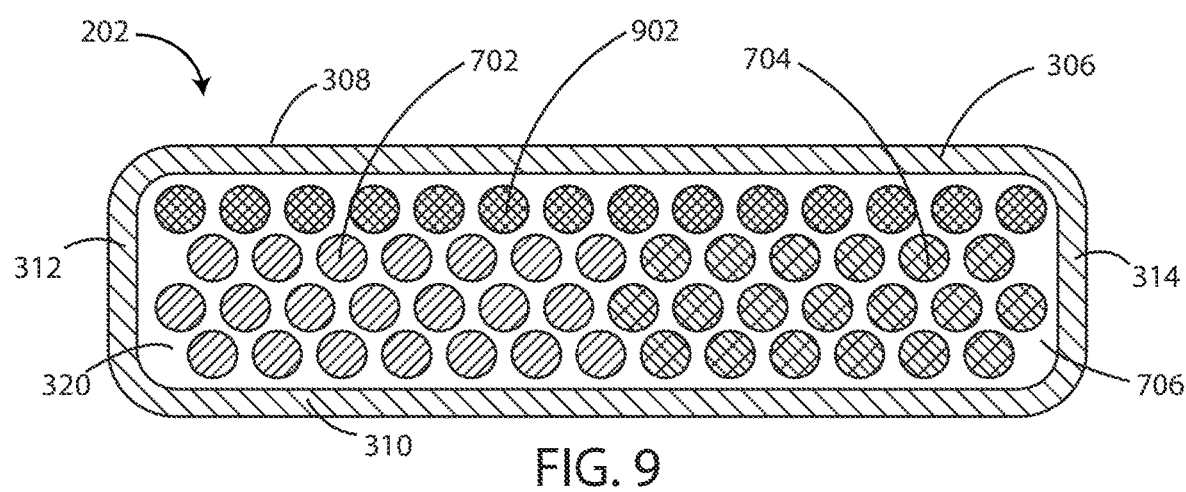
FIG. 9 is a schematic cross-sectional view of a sensing element in accordance with additional embodiments herein.

Referring now to FIGS. 7-9, sensing element 202 is shown in accordance with various embodiments herein. As discussed above with reference to FIG. 3, sensing element 202 can include an outer barrier layer 306. Outer barrier layer 306 can form a top 308, a bottom 310, and opposed sides 312 and 314 to surround an interior volume 320 of sensing element 202.

In particular, FIG. 7 shows a sensing element 202 having an outer barrier layer 306, the entirety of which can be formed from a polymeric matrix permeable to sodium ions, potassium ions, and hydronium ions, and the like. Polymeric matrix materials suitable for use in the outer barrier layer 306 are discussed further below.

The sensing element(s) 202 embodied herein can include an interior volume 320 and can also include various indicator beads for detecting an ion concentration of a bodily fluid when implanted in the body disposed within an interior volume 320. For example, FIG. 7 shows a first indicator bead 702 and a second indicator bead 704. The first and second indicator beads 702 and 704 can include a polymeric support material and one or more ion selective sensing components as described more fully below. Physiological analytes such as potassium ion, sodium ion, hydronium ion, and the like, can diffuse through the top 308 of the outer barrier layer 306 and onto and/or into first and second indicator beads 702 and 704 where they can bind with the ion selective sensors to produce a fluorimetric or colorimetric response. In some embodiments, first indicator bead 702 can be designed to detect a control analyte. In some embodiments, the first indicator beads 702 can be segregated to one side of the interior volume 320, with or without an interior divider. In some embodiments, second indicator bead 704 can be designed to detect the test analyte. In some embodiments, the second indicator beads 704 can be segregated to a different side of the interior volume than the first indicator beads 702. In some embodiments the first indicator beads 702 and the second indicator beads 704 can be separated out by having two individual outer barriers 306. For example, instead of a single outer barrier 306, there can be two discrete outer barriers 306 with each surrounding a separate set of indicator beads. In various embodiments, the two sets of beads can be spaced out by a certain distance, such as at least about 0.1, 0.2, 0.3, 0.4, 0.5, 1, 2, 3, 5, 10 or 15 millimeters and less than 100, 70, 50, 40, 30, or 20 millimeters.

Beyond diffusion through the top, in some embodiments additional diffusion of physiological analytes is also possible through bottom 310 and opposing sides 312 and 314.

While FIG. 7 shows discrete indicator beads, it will be appreciated that the indicator components can also exist in other forms such as a single larger mass or the like.

In some embodiments, the sensing element(s) 202 embodied herein can include an aqueous solution 706 disposed within the interior volume 320. In some embodiments, the aqueous solution 706 can include potassium ions at a concentration of about 3.0 to about 6.0 mmol/L. In some embodiments, the aqueous solution 706 can include potassium ions at a concentration of about 1.0, 2.0, 3.0, 4.0, 5.0, 6.0, 7.0, or 8.0 mmol/L. In some embodiments, the concentration of potassium ions in the aqueous solution 706 can be in a range between any of the foregoing multiples provided that the upper bound of the range is greater than the lower bound of the range.

It will be appreciated that some portions of the outer barrier layer can be formed of a different material, while in other embodiments the entire outer barrier layer is all formed of the same material. FIG. 8 shows an embodiment of sensing element 202 having an outer barrier layer 306, the top 308 being the only portion formed from a polymeric matrix permeable to sodium ions, potassium ions, and hydronium ions, and the like. In this embodiment, the bottom 310, and opposing sides 312 and 314 of the outer barrier layer 306 shown in FIG. 8 can be formed from a non-porous material, such as a metal, metal alloy, polymer, ceramic, and the like. It will be appreciated that bottom 310 can be formed of a transparent material to facilitate optical communication with the optical excitation 302 and optical detection 304 assemblies. In some embodiments, the bottom 310 can include a transparent aperture.

FIG. 9 shows an embodiment of sensing element 202 having an outer barrier layer 306 like those shown in FIGS. 7 and 8. It will be appreciated that outer barrier layer 306 of FIG. 9 can be formed of a porous material or formed partially of a porous and partially of a non-porous material. It will be appreciated that bottom 310 of outer barrier layer 306 can be formed of a transparent material to facilitate optical communication with the optical excitation 302 and optical detection 304 assemblies.

As shown in FIG. 9, sensing element 202 can include active-agent releasing particles 902 disposed within the interior volume of the outer barrier layer. In some embodiments, the active agent disposed within active-agent releasing particles 902 can have anti-inflammatory effects. In some embodiments, the active agent disposed within active-agent releasing particles 902 can have angiogenic effects. In some embodiments, release properties of the active agent disposed within active-agent releasing particles 902 can be varied over the course of time. In some embodiments, release properties of the active-agent releasing particles 902 can include a first particle type configured to release an anti-inflammatory agent during a first period of time and a second particle type configured to release an angiogenic agent after the passage of the first period of time. The first period of time can be 0 to 2 weeks, 0 to 3 weeks, 0 to 4 weeks, 0 to 6 weeks, 0 to 8 weeks, 0 to 10 weeks, 0 to 12 weeks, or other time periods.

Figure 10:
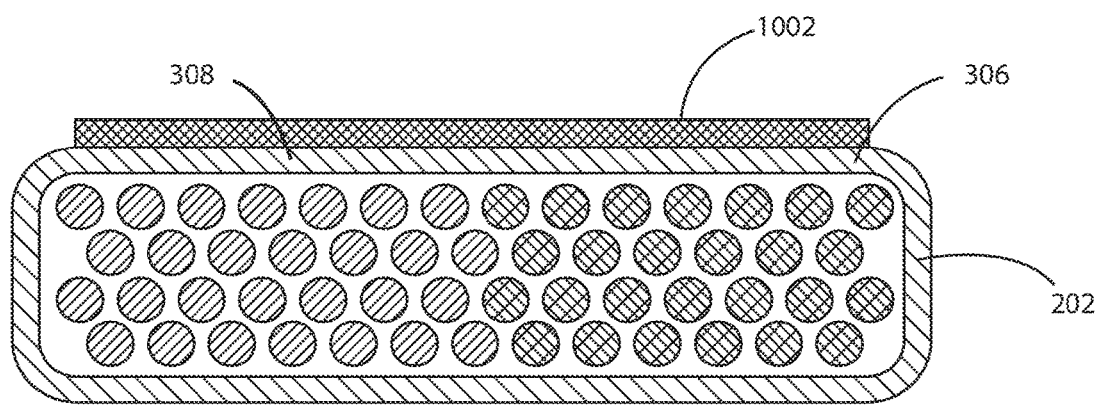
FIG. 10 is a schematic cross-sectional view of a sensing element in accordance with additional embodiments herein.

Referring now to FIG. 10, an embodiment of chemical sensor 106 is shown having a porous overcoat layer 1002 disposed over the top 308 of the sensing element 202. Porous overcoat layer 1002 can be permeable to sodium ions, potassium ions, hydronium ions, and the like. Porous overcoat layer 1002 can be formed of various porous materials including, but not limited to, porous polymers, porous ceramics, porous glasses, porous metals, porous composites and the like. An active agent, such as those described elsewhere herein can be disposed within the porous overcoat layer 1002 can be configured to diffuse out after the device is implanted. In some embodiments, an active agent is disposed in the porous overcoat layer 1002 and not within the underlying top 308 of the outer barrier layer 306 of the sensing element 202.

Figure 11:
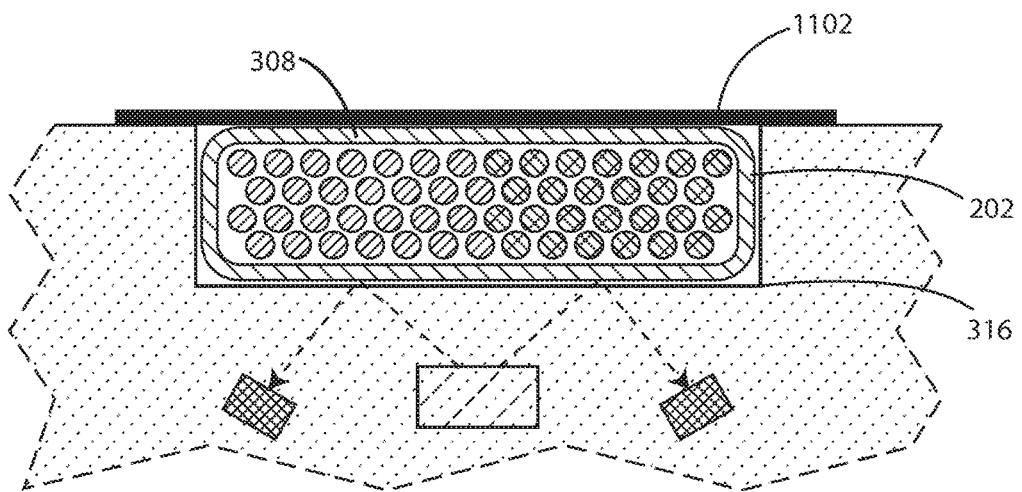
FIG. 11 is a schematic cross-sectional view of a chemical sensor in accordance with additional embodiments herein.

In some embodiments, it can be desirable to isolate the chemical sensor from ambient light that may otherwise enter the chemical sensor. Referring now to FIG. 11, an embodiment of chemical sensor 106 is shown having an opaque cover layer 1102 disposed on the top 308 of the sensing element 202. In some embodiments, opaque cover layer 1102 can optically isolate sensing element 202 from the tissues surrounding the chemical sensor in vivo, so as to prevent interference from background light scatter. The porous overcoat layer 1102 can include a polymeric material with an opacifying agent. Exemplary opacifying agents can include carbon black, or carbon-based opacifying agents, ferric oxide, metallic phthalocyanines, and the like. In some embodiments, the opacifying agent can be carbon black. Opacifying agents can be dispersed in the porous overcoat layer 1102, or in a separate layer, in an amount effective to provide the desired degree of opacity to provide the desired optical isolation.

Figure 12:
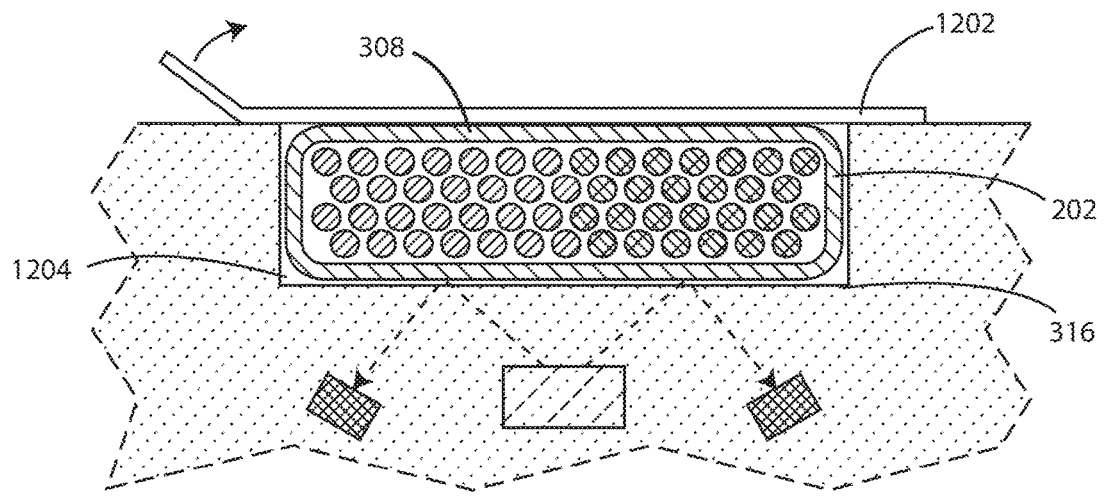
FIG. 12 is a schematic cross-sectional view of a chemical sensor in accordance with additional embodiments herein.

In some embodiments, it may be desirably to ship the chemical sensor and/or medical device with the sensor pre-wetted (e.g., bathed in an aqueous solution). Referring now to FIG. 12, an embodiment of chemical sensor 106 is shown having a seal 1202 over the top 308 of sensing element 202. Seal 1202 can provide a tight seal between the external environment and the chemical sensor 106 when packaged. For example, seal 1202 can provide an effective barrier to keep aqueous solution 1204 within recessed pan 316 such that the sensing element 202 can be constantly bathed in aqueous solution 1204 prior to implant.

In some embodiments, the aqueous solution 1204 present in recessed pan 316 can also include potassium ions at a concentration of about 3.0 to about 6.0 mmol/L. In some embodiments, the aqueous solution 1204 can include potassium ions at a concentration of about 1.0, 2.0, 3.0, 4.0, 5.0, 6.0, 7.0, or 8.0 mmol/L. In some embodiments, the concentration of potassium ions in the aqueous solution 1204 can be in a range between any of the foregoing amounts provided that the upper bound of the range is greater than the lower bound of the range.

Seal 1202 can be removed from the chemical sensor 106 by a medical professional just prior to implantation. In some embodiments, seal 1202 can be non-porous to the passage of aqueous solutions. In some embodiments, seal 1202 can be made from a polymer such as polyethylene terephthalate (PET), polytetrafluoroethylene (PTFE), polyethylene, polystyrene, and the like. In some embodiments, the seal 1202 can be made from a foil, such as a metal foil. In some embodiments, the seal 1202 can be made from a radiopaque material.

Figure 13:
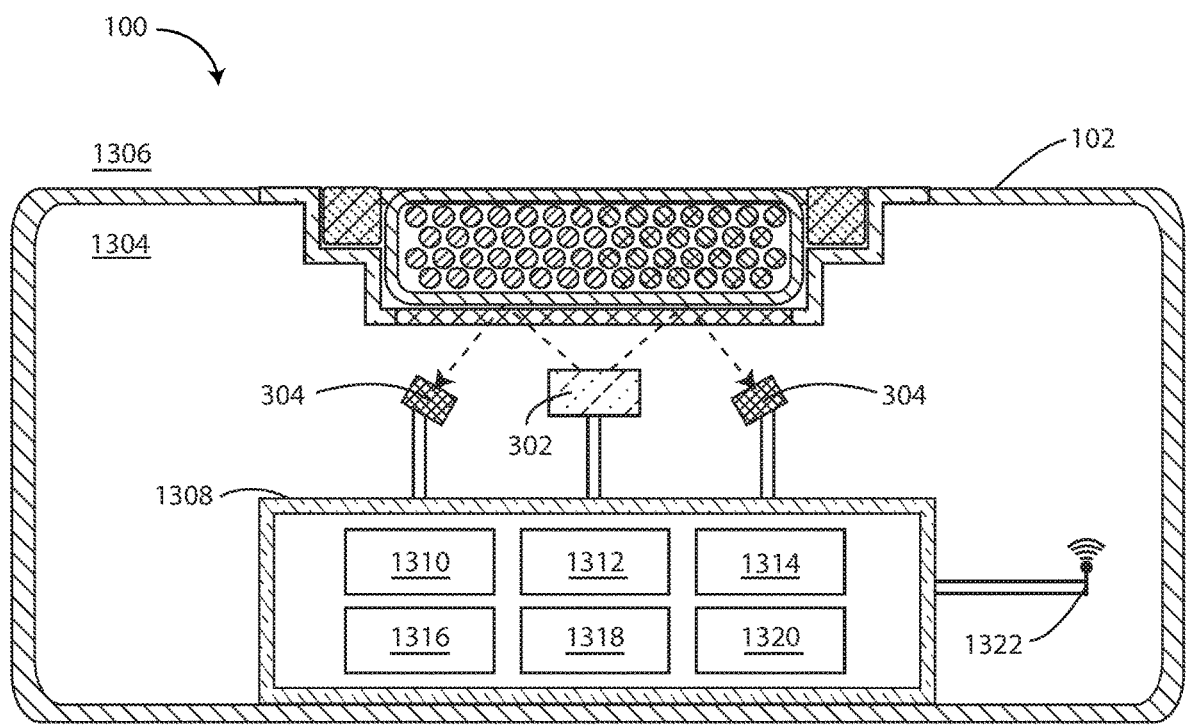
FIG. 13 is a schematic cross-sectional view of an implantable medical device in accordance with various embodiments herein.

Referring now to FIG. 13, a schematic cross-sectional view of IMD 100 is shown in accordance with various embodiments herein. The IMD 100 can include implantable housing 102. The implantable housing 102 of IMD 100 can include various materials such as metals, polymers, ceramics, and the like. In some embodiments, the implantable housing 102 can be a single integrated unit. In other embodiments, the implantable housing 102 can include implantable housing 102 and epoxy header 104, as discussed above. In some embodiments, the implantable housing 102, or one or more portions thereof, can be formed of titanium. In some embodiments, one or more segments of the implantable housing 102 can be hermetically sealed.

Implantable housing 102 can define an interior volume 1304 that in some embodiments is hermetically sealed off from the area 1306 outside of IMD 100. The IMD 100 can include circuitry 1308. Circuitry 1308 can include various components, such as components 1310, 1312, 1314, 1316, 1318, and 1320. In some embodiments, these components can be integrated and in other embodiments these components can be separate. In some embodiments, the components can include one or more of a microprocessor, memory circuitry (such as random access memory (RAM) and/or read only memory (ROM)), recorder circuitry, telemetry circuitry, chemical sensor interface circuitry, power supply circuitry (which can include one or more batteries), normalization circuitry, chemical sensor control circuitry, and the like. In some embodiments recorder circuitry can record the data produced by the chemical sensor and record time stamps regarding the same. In some embodiments, the circuitry can be hardwired to execute various functions, while in other embodiments the circuitry can be implemented as instructions executing on a microprocessor or other computation device.

A telemetry interface 1322 can be provided for communicating with external devices such as a programmer, a home-based unit, and/or a mobile unit (e.g., a cellular phone, portable computer, etc.). In some embodiments telemetry interface 1322 can be provided for communicating with implanted devices such as a therapy delivery device (e.g. a pacemaker, cardiovertor-defibrillator) or monitoring-only device (e.g. an implantable loop recorder). In some embodiments, the circuitry can be implemented remotely, via either near-field, far-field, conducted, intra-body or extracorporeal communication, from instructions executing on any of the external or the implanted devices, etc. In some embodiments, the telemetry interface 1322 can be located within implantable housing 102. In some embodiments, the telemetry interface 1322 can be located in header 104.

The optical excitation 302 and optical detection 304 assemblies of the chemical sensor 106 can be in electrical communication with the circuitry 1308 within the interior volume 1304. In some embodiments, the control circuitry 1308 is configured to selectively activate the optical excitation 302 and optical detection 304 assemblies of the chemical sensor 106.

Figure 14:
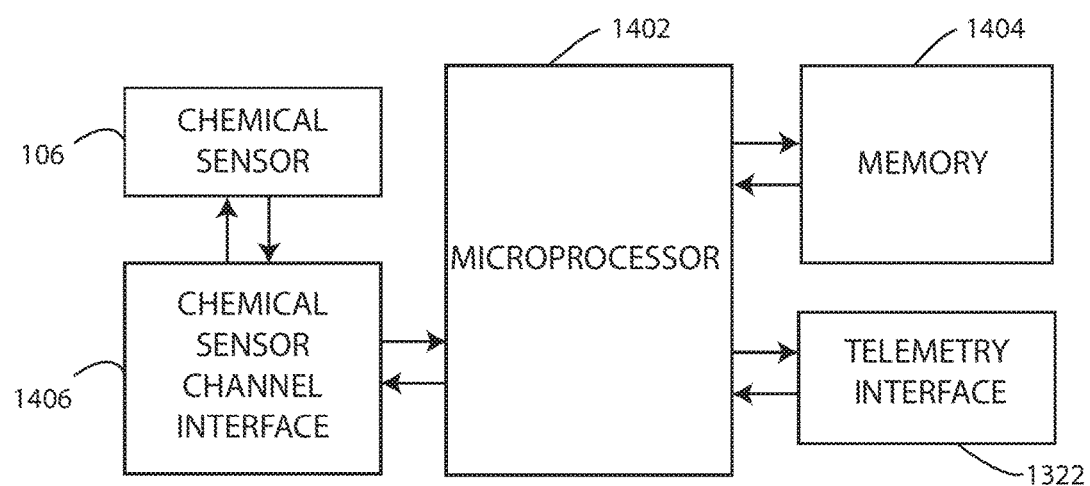
FIG. 14 is a schematic diagram of components of an implantable medical device in accordance with various embodiments herein.

Referring now to FIG. 14, a schematic diagram of components of IMD 100 in accordance with various embodiments herein. It will be appreciated that some embodiments can include additional elements beyond those shown in FIG. 14. In addition, some embodiments may lack some elements shown in FIG. 14. IMD 100 can gather information through one or more sensing channels. A microprocessor 1402 can communicate with a memory 1404 via a bidirectional data bus. The memory 1404 can include read only memory (ROM) or random access memory (RAM) for program storage and RAM for data storage, or any combination thereof. The implantable medical device can also include one or more chemical sensors 106 and one or more chemical sensor channel interfaces 1406 which can communicate with a port of microprocessor 1402. The chemical sensor channel interface 1406 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like. A telemetry interface 1322 is also provided for communicating with external devices such as a programmer, a home-based unit, and/or a mobile unit (e.g., a cellular phone, portable computer, etc.), implanted devices such as a pacemaker, cardiovertor-defibrillator, loop recorder, and the like.

Ion-Permeable Polymeric Matrix Materials

As referenced above, the outer barrier layer of the sensing element can be formed of an ion-permeable polymeric matrix material in some embodiments. Suitable polymers for use as the ion-permeable polymeric matrix material can include, but are not limited to polymers forming a hydrogel. Hydrogels herein can include homopolymeric hydrogels, copolymeric hydrogels, and multipolymer interpenetrating polymeric hydrogels. Hydrogels herein can specifically include nonionic hydrogels. In some embodiments, hydrogels herein can be prepared from polymerization of various monomers or macromers including one or more of 2-hydroxyethyl methacrylate (HEMA), 2-hydroxypropyl methacrylate (HPMA), acrylamide, acrylic acid, N-isopropylacrylamide (NIPAm), methoxyl polyethylene glycol monoacrylate (PEGMA), and the like. In some embodiments, polymers can include, but are not limited to polyhydroxyethyl methacrylate (HEMA), cellulose, polyvinyl alcohol, dextran, polyacrylamides, polyhydroxyalkyl acrylates, polyvinyl pyrrolidones, and mixtures and copolymers thereof. In some embodiments, suitable polymers for use with the ion-permeable polymeric matrix described herein include those that are transparent.

Active Agents

The active agent can be any drug or bioactive agent which can serve as a useful therapeutic, prophylactic, or even diagnostic agent when released into the patient. Exemplary bioactive agents include, but are not limited to, the following: an anti-inflammatory; anti-proliferative; anti-arrhythmic; anti-migratory; anti-neoplastic; antibiotic; anti-restenotic; anti-coagulation; anti-infectives; anti-oxidants; anti-macrophagic agents (e.g., bisphosphonates); anti-clotting (e.g., heparin, coumadin, aspirin); anti-thrombogenic; immunosuppressive agents; an agent that promotes healing; steroids (e.g., a glucocorticosteroid)); and combinations thereof.

Suitable active agents for use with the embodiments herein can specifically include, but are not limited to anti-inflammatory agents. In some embodiments, suitable anti-inflammatory agents can include steroids generally and, in specific, corticosteroids. In some embodiments, the anti-inflammatory agent can include ketorolac, dexamethasone, hydrocortisone, prednisolone, methylprednisolone, indomethacin, diclofenac, ketoprofen, piroxicam, metamizol magnesium and the like. In some embodiments, anti-inflammatory agents can be configured to be eluted shortly after implantation of the device.

In some embodiments, suitable active agents can also include angiogenic agents, to promote the in-growth of capillaries. In some embodiments, angiogenic agents can be configured to be eluted at a later time (e.g., following elution of an anti-inflammatory at an earlier point in time) to promote the ingrowth of capillaries to the chemical sensor.

In some embodiments, suitable angiogenic agents can include growth factors such as vascular endothelial growth factor (VEGF), fibroblast growth factor (FGF), platelet-derived growth factor (PDGF), and the like. In some embodiments, the additional active agents can include immobilized heparin to prevent blot clot formation.

Active agents herein can be in various forms including in a solution, as a suspension, as a particulate, or the like.

Active Agent Eluting Materials

Various embodiments herein can include an active agent eluting material or matrix. The active agent eluting material can serve to provide a matrix into which the active agent can be disposed and from which the active agent can elute after the chemical sensor and/or medical device is implanted within the body of a patient. However, in other embodiments, the active agent can be disposed with or without an eluting material or matrix and in or on portions of the sensing element or other portions of the device including, but not limited to, the top, bottom, or opposed sides of the barrier layer, in depots adjacent to the sensing element, in a channel around the sensing element, above the sensing element, below the sensing element, to the sides of the sensing element, inside of the sensing element and the like.

The active agent eluting material can include, but is not limited to, one or more of the following polymers: SOLEF® (SOLEF® 21508 polymer); polyvinylidene-hexafluoropropylene or poly(VF2-co-HFP) from Solvay, Brussels, Belgium; acetoxy, cure, Room-Temperature-Vulcanizing (RTV) silicone elastomers; UV curable silicone; UV curable polymer; platinum catalyzed addition cure liquid silicone rubber; styrene isobutylene styrene (SIBS); peroxide cure silicone rubber; Nafion; silicone (including LSR), polymers based on the structural unit $R_2SiO$, where R is an organic group; medical adhesives; cyanoacrylates; Rehau 1511; ethylene vinyl alcohol (E/VAL; a thermoplastic polymer); polyethylene glycol (PEG); polyvinyl alcohol; polyvinyl propylene; hyaluronic acid; polyacrylamides; polycaprolactone, polylactide (PLA); polyglycolide (PGA); poly(lactide-co-glycolide) (PLGA); polyurethane; polymethylmethacrylates; polyethylene; polyvinylpyrrolidone; polyacrylic acid; poly (2-hydroxyethyl methacrylate); pHEMA polyacrylamide; polyethylene-co-vinyl acetate; polyanhydrides; polyorthoesters; polyimides; polyamides; polyanhydrides; polyetherketones; polyaryletherketones; polysiloxane urethanes; polyisobutylene copolymers; and copolymers and combinations thereof.

The active agent eluting material can be in various forms including, but not limited to, depots, spots, discrete particles, layers, as a filling, as a particulate within other materials herein such as materials forming at least a portion of the barrier layer, and the like.

Optical Excitation and Detection Assemblies

In some embodiments, the optical excitation assembly 302 can include solid state light sources such as GaAs, GaAlAs, GaAlAsP, GaAlP, GaAsP, GaP, GaN, InGaAlP, InGaN, ZnSe, or SiC light emitting diodes or laser diodes that excite the sensing element(s) 202 at or near the wavelength of maximum absorption for a time sufficient to emit a return signal. However, it will be understood that in some embodiments the wavelength of maximum absorption/reflection varies as a function of concentration in the colorimetric sensor.

In some embodiments, the optical excitation assembly 302 can include other light emitting components including incandescent components. In some embodiments, the optical excitation assembly 302 can include a waveguide. The optical excitation assembly 302 can also include one or more bandpass filters, high pass filter, low pass filter, antireflection elements, and/or focusing optics.

In some embodiments, the optical excitation assembly 302 can include a plurality of LEDs with bandpass filters, each of the LED-filter combinations emitting at a different center frequency. According to various embodiments, the LEDs can operate at different center-frequencies, sequentially turning on and off during a measurement, illuminating the sensing element 202. As multiple different center-frequency measurements are made sequentially, a single unfiltered detector can be used in some embodiments. However, in some embodiments, a polychromatic source can be used with multiple detectors that are each bandpass filtered to a particular center frequency.

The sensing element 202 can include one or more types of indicator beads having embedded therein various types of ion selective sensors. Physiological analytes of interest can diffuse into and out of the sensing element 202 and bind with an ion selective sensor to result in a fluorimetric or colorimetric response. Reference analytes can similarly diffuse into and out of the sensing element 202 and serve as a control sample. Exemplary ion selective sensors are described more fully below.

The optical detection assembly 304 can be configured to receive light from the sensing element 202. In an embodiment, the optical detection assembly 304 can include a component to receive light. By way of example, in some embodiments, the optical detection assembly 304 can include a charge-coupled device (CCD). In other embodiments, the optical detection assembly 304 can include a photodiode, a junction field effect transistor (JFET) type optical sensor, or a complementary metal-oxide semiconductor (CMOS) type optical sensor. In some embodiments, the optical detection assembly 304 can include an array of optical sensing components. In some embodiments, the optical detection assembly 304 can include a waveguide. The optical detection assembly 304 can also include one or more bandpass filters and/or focusing optics. In some embodiments, the optical detection assembly 304 can include one or more photodiode detectors, each with an optical bandpass filter tuned to a specific wavelength range.

The optical excitation and detection assemblies, 302 and 304, respectively, can be integrated using bifurcated fiber-optics that direct excitation light from a light source to one or more sensing elements 202, or simultaneously to sensing element(s) 202 and a reference channel. Return fibers can direct emission signals from the sensing element(s) 202 and the reference channels to one or more optical detector assemblies 304 for analysis by a processor, such as a microprocessor. In some embodiments, the optical excitation and detection assemblies are integrated using a beamsplitter assembly and focusing optical lenses that direct excitation light from a light source to the sensing element and direct emitted or reflected light from the sensing element to an optical detector for analysis by a processor.

Ion Selective Sensors

In accordance with the embodiments herein, sensing elements 202 can include one or more ion selective sensors. Ion selective sensors may either rely on surface phenomena or on concentration changes inside the bulk of a phase. Ion selective sensors can include optical sensors, including both non-carrier optical sensors and carrier-based optical sensors, and ion-selective electrodes (ISEs). In some embodiments, the ion selective sensor is fluorimetric, and can include a complexing moiety and a fluorescing moiety. Fluorimetric ion selective sensors can exhibit differential fluorescent intensity based upon the complexing of an analyte to a complexing moiety. In some embodiments, the ion selective sensor can be colorimetric, and can include a complexing moiety and a colorimetric moiety. Colorimetric ion selective sensors can exhibit differential light absorbance based upon the complexing of an analyte to a complexing moiety.

In some embodiments, the ion selective sensor comprises a non-carrier or carrier-based fluorescent or colorimetric ionophoric composition that comprises a complexing moiety for reversibly binding an ion to be analyzed, and a fluorescing or colorimetric moiety that changes its optical properties as the complexing agent binds or releases the ion. The complexing agents of the invention can optionally be appended with one or more organic substituents chosen to confer desired properties useful in formulating the ion sensing composition. By way of example, the substituents can be selected to stabilize the complexing agent with respect to leaching into the solution to be sensed, for example, by incorporating a hydrophobic or polymeric tail or by providing a means for covalent attachment of the complexing agent to a polymer support within the ion selective sensor.

In some embodiments, the sensing element can include ion selective sensors such as an ionophore or a fluoriono-phore. Suitable ionophores for use with the embodiments herein can include, but not be limited to, sodium specific ionophores, potassium specific ionophores, calcium specific ionophores, magnesium specific ionophores, and lithium specific ionophores. Suitable fluorionophores for use with the embodiments herein can include, but not be limited to, lithium specific fluoroionophores, sodium specific fluoroionophores, and potassium specific fluoroionophores.

Exemplary ion selective sensors and methods for their use are disclosed in commonly assigned U.S. Pat. No. 7,809,441, the contents of which is herein incorporated by reference in its entirety.

The embodiments described herein are not intended to be exhaustive or to limit the invention to the precise forms disclosed in the following detailed description. Rather, the embodiments are chosen and described so that others skilled in the art can appreciate and understand the principles and practices. Aspects have been described with reference to various specific and preferred embodiments and techniques. However, it should be understood that many variations and modifications may be made while remaining within the spirit and scope herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The invention claimed is:

1. An implantable medical device comprising:
   a chemical sensor configured to detect an ion concentration in a bodily fluid, the chemical sensor comprising:
      a sensing element, the sensing element comprising
         an outer barrier layer forming a top, a bottom, and opposed sides of the sensing element, the top of the outer barrier layer comprising a polymeric matrix permeable to analytes; and
         one or more ion selective sensors;
   an optical excitation assembly configured to illuminate the sensing element;
   and an optical detection assembly configured to receive light from the sensing element;
   a drug-eluting material with an active agent disposed therein positioned around the opposed sides of the sensing element, the active agent comprising an active agent having anti-inflammatory effects; and
   an implantable housing, the chemical sensor and the drug-eluting material coupled to the implantable housing, the implantable housing defining a multi-tiered recessed pan into which the sensing element fits into a lower tier of the multi-tiered recessed pan and the drug-eluting material fits into an upper tier of the multi-tiered recessed pan, wherein the lower tier is disposed deeper in the multi-tiered recessed pan then the upper tier, such that a top surface of the multi-tiered recessed pan is substantially flush with a top of the sensing element and a top surface of the drug-eluting material, the drug-eluting material with an active agent disposed therein forming a ring around the sensing element.

2. The implantable medical device of claim 1, the drug-eluting material with an active agent disposed therein forming one or more discrete depots around the sensing element.

3. The implantable medical device of claim 1, further comprising an active agent disposed within a portion of the sensing element.

4. The implantable medical device of claim 1, the lower tier of the multi-tiered recessed pan comprising a transparent member.

\* \* \* \* \*